(12) United States Patent
Wimberger-Friedl et al.

(10) Patent No.: US 9,435,722 B2
(45) Date of Patent: Sep. 6, 2016

(54) FILTERING PARTICLES FROM BLOOD OR OTHER MEDIA

(71) Applicant: KONINKLIJKE PHILIPS N.V., Eindhoven (NL)

(72) Inventors: Reinhold Wimberger-Friedl, Veldhoven (NL); Anja Van De Stolpe, Vught (NL); Freek Van Hemert, Dordrecht (NL)

(73) Assignee: Koninklijke Philips N.V., Eindhoven (NL)

( * ) Notice: Subject to any disclaimer, the term of this patent is extended or adjusted under 35 U.S.C. 154(b) by 13 days.

(21) Appl. No.: 14/353,512

(22) PCT Filed: Oct. 24, 2012

(86) PCT No.: PCT/IB2012/055844
§ 371 (c)(1),
(2) Date: Apr. 23, 2014

(87) PCT Pub. No.: WO2013/061257
PCT Pub. Date: May 2, 2013

(65) Prior Publication Data
US 2014/0302529 A1    Oct. 9, 2014

Related U.S. Application Data

(60) Provisional application No. 61/550,947, filed on Oct. 25, 2011.

(30) Foreign Application Priority Data

Nov. 10, 2011 (EP) .................................... 11188536

(51) Int. Cl.
*G01N 1/40* (2006.01)
*G01N 1/18* (2006.01)
(Continued)

(52) U.S. Cl.
CPC ...... *G01N 1/4077* (2013.01); *G01N 33/54326* (2013.01); *G01N 33/57492* (2013.01); *G01N 2001/4088* (2013.01); *Y10T 436/25375* (2015.01)

(58) Field of Classification Search
CPC ................. G01N 1/40; G01N 1/4077; G01N 2001/4088; G01N 33/54326; G01N 33/57492; Y10T 436/25; Y10T 436/25375; Y10T 436/2575
USPC ................. 436/63, 164, 165, 174, 177, 180; 422/82.05, 527, 534, 554; 435/4, 29, 435/30, 325, 7.23, 287.1, 287.2, 288.7, 435/309.1; 210/767, 768, 222
See application file for complete search history.

(56) References Cited

U.S. PATENT DOCUMENTS 4,790,640 A * 12/1988 Nason ............... B01L 3/502707
                                                                  156/99
6,319,719 B1 * 11/2001 Bhullar ............. B01L 3/502746
                                                                  422/73
(Continued)

FOREIGN PATENT DOCUMENTS

| EP | 1459733 | 3/2004 |
|----|---------|--------|
| WO | WO9700121 | 1/1997 |
| WO | WO2011081530 | 7/2011 |

OTHER PUBLICATIONS

G. Vona, et al., "Isolation by Size of Epithelial Tumor Cells; A New Method for the Immunomorphological and Molecular Characterization of Circulating Tumor Cells", American Journal of Pathology, Jan. 2000, vol. 156, pp. 57-63 (downloaded from internet).

*Primary Examiner* — Maureen Wallenhorst (57) ABSTRACT

A filter element and method for retaining particles of a medium, for example rare cells of blood. The filter element includes at least one opening that has an elongate cross section and/or a cross section that decreases in a flow direction. The filter element may be bordered by a transparent wall. The filter element may be provided with a plurality of elongate openings of a stepwise decreasing cross section that are arranged on a common transparent slide. The filter element permits high flow rates to be realized throughout the filtering process and the retained particles are immediately ready for visual inspection without a need for a further transfer.

15 Claims, 2 Drawing Sheets

(51) Int. Cl.
*G01N 33/543* (2006.01)
*G01N 33/574* (2006.01)

(56) References Cited

U.S. PATENT DOCUMENTS

| | | |
|---|---|---|
| 2002/0137052 A1 | 9/2002 | Bridgham et al. |
| 2008/0000833 A1 | 1/2008 | Peters et al. |
| 2009/0010673 A1 | 1/2009 | Iida |
| 2009/0014360 A1* | 1/2009 | Toner .................. B01D 21/0087 209/208 |
| 2013/0121895 A1* | 5/2013 | Tang ........................ B01F 5/102 422/527 |
| 2013/0130226 A1* | 5/2013 | Lim .................... B01L 3/50273 435/2 |

* cited by examiner

FILTERING PARTICLES FROM BLOOD OR OTHER MEDIA

CROSS-REFERENCE TO PRIOR APPLICATIONS

This application is the U.S. National Phase application under 35 U.S.C. §371 of International Application Serial No. PCT/IB2012/055844, filed on Oct. 24, 2012, which claims the benefit of U.S. Application Ser. No. 61/550,947, filed on Oct. 25, 2011 and European Application Serial No. 11188536.4, filed on Nov. 11, 2011. These applications are hereby incorporated by reference herein.

FIELD OF THE INVENTION

The invention relates to methods, filter elements, and filter systems for retaining particles of a medium, particularly for retaining cells from a biological fluid like blood other bodily fluids.

BACKGROUND OF THE INVENTION

Rare cell isolation is an important example of an application in which particles (the rare cells) are filtered from a medium (blood). In conventional filters used for this purpose, a plurality of pores is arranged in a layer that extends perpendicular to the flow direction of the filtered medium. A disadvantage of such filters is that the retained cells are often damaged due to high pressure gradients. Moreover, a transfer of the cells is needed if they shall be further analyzed, which means additional stress for the cells.

SUMMARY OF THE INVENTION

It is an object of the invention to provide means that allow for an improved filtering of particles from a medium, particularly for the filtering of (rare) cells from a biological fluid like blood other bodily fluids (e.g. aspirates).

This object is achieved by filter elements according to claims 1, 2, 3, and 5, by methods according to claims 4, 6 and 15, and by filter systems according to claims 12 and 13. Preferred embodiments are disclosed in the dependent claims.

A filter element according to a first aspect of the invention serves for retaining particles of a medium flowing in a flow direction through at least one opening of the filter element.

In this context, the term "particle" shall denote any connected piece of material contained by the medium, for example a (macro-)molecule, a piece of a solid body, a biological cell, a microorganism, or a part thereof. The diameter of the particles of interest will typically be about 1 μm or larger. Moreover, the "flow direction" shall by definition be determined within the opening, in particular at the geometrical centre of the opening and/or as an average across the whole opening (if it is not constant throughout the whole opening).

The filter element according to the first aspect of the invention shall have at least one opening with an elongate cross section wherein the ratio between the maximal and the minimal diameter of the cross section is preferably larger than 2:1, more preferably larger than 5:1. The "cross section" is by definition measured perpendicular to the flow direction. If the opening has different cross sections at different positions of the flow direction, all these encountered cross sections shall be elongate. Moreover, the cross section can in general have any arbitrary (connected) shape; typically, the shape will however be convex (e.g. elliptical or polygonal).

As the function as a "filter element" indicates, the opening of the filter element shall be some kind of bottleneck in the flow path of the medium, i.e. the flow path shall be wider in front of and typically also behind such an opening. Accordingly, the particles of interest will be retained in the opening of the filter element and nowhere else. In particular, the cross section or clearance in the flow path from a sample inlet to the opening shall be larger than within the opening. Moreover, each opening is preferably preceded by a distribution chamber from which incoming sample medium is led into the opening. Similarly, each opening may be followed by a collection chamber which receives sample medium after its passage through the opening, wherein said distribution and collection chambers have a larger clearance than the opening. In absolute figures, the clearance of the opening (i.e. the maximal diameter of a sphere that fits through the opening) typically ranges between about 1 μm and 50 μm. It is chosen depending on the application at hand. In case of blood filtering, the clearance should for example allow for the free passage of erythrocytes.

A method that is related to the first aspect of the invention serves for filtering particles out of a medium by retaining them in at least one opening through which said medium passes in a flow direction. This method is characterized in that the retained particles are held between opposite areas (or points) where they contact the opening, wherein the medium continues to flow along said particles outside said areas, through the remaining parts of the opening. Such a retention of particles can particularly be achieved with the elongate opening of the above filter element, in which a particle gets stuck between the opposite narrow walls of the opening.

The filter element and the method according to the first aspect of the invention have the advantage that mechanical stress for a retained particle is minimized because the particle does not completely block the filter opening. Instead, there will always be space left through which the medium can continue to flow, which prevents the generation of excessive pressure gradients between the back and the front side of the particles. Moreover, flow through the filter element can continue at a high rate because no complete opening is blocked.

According to a second aspect, the invention relates to a filter element for retaining particles of a medium flowing in a flow direction through at least one opening, wherein said opening has a cross section that decreases (narrows) in flow direction. Preferably, this decrease amounts to more than about 20%, i.e. the minimal diameter of the cross section at the exit of the opening is at most 80% of the minimal diameter of the cross section at the entrance of the opening. Still more preferably, the decrease is more than about 50%.

A method that is related to the second aspect of the invention serves for filtering particles out of a medium by retaining them in at least one opening through which said medium passes in a flow direction. This method is characterized in that the particles are retained at different positions (seen in flow direction) which correspond to a (passage related) property of said particles. Said property typically comprises the size, stiffness and/or surface functionality of said particles which can lead to the capture of a particle at a certain position. The method can particularly be executed with the aforementioned filter element, because the decreasing cross section of the opening retains particles of different sizes at different positions.

The filter element and the method according to the second aspect of the invention have the advantage that they "automatically" arrange the retained particles in a spatial order corresponding to their size. As biological cells of different types usually differ in size and rigidity (compliance), it is thus possible to spatially separate cell fractions, which is advantageous for further analysis steps.

In order to achieve a significant spatial spread of different particles, the opening may preferably have a length (measured in flow direction) that is more than about five times the smallest minimal diameter of all cross sections.

According to a third aspect, the invention relates to a filter element for retaining particles of a medium flowing in flow direction through at least one opening, wherein said opening is bordered by a transparent wall. The transparent wall will typically extend parallel to the flow direction and form at least a part of the material in which the opening is formed.

A method that is related to the third aspect of the invention serves for filtering particles out of a medium by retaining them in at least one opening through which said medium passes in a flow direction. This method is characterized in that the particles are optically inspected from a direction oblique—preferably substantially perpendicular—to the flow direction of the medium. The method can particularly be executed in the aforementioned filter element in which the transparent wall allows visual inspection of the interior of the opening. If the opening has an elongated cross section, the optical inspection may favorably also be oblique (e.g. substantially perpendicular) to the large dimension of the opening.

The filter element and the method according to the third aspect of the invention have the advantage that the particles which are retained in the opening can directly be observed. Hence there is no need to transfer these particles from the filter element to another location prior to such an observation. This simplifies the workflow and, most of all, means less stress for the particles.

It should be noted that due to the relatedness between the filter elements and the methods according to the various aspects of the invention, explanations and definitions provided for one of these embodiments are valid for the other ones, too.

The features of the filter elements and/or the methods defined above may preferably be applied in any combination. In particular, it is preferred that a filter element for retaining particles of a medium has at least one opening with an elongate cross section that decreases in flow direction, wherein said opening is bordered by a transparent wall.

Similarly, a method is preferred in which filtering of particles out of a medium is achieved by retaining them in at least one opening, wherein said particles are retained at different positions that correspond to their size, wherein the retained particles are held between opposite areas while the medium continues to flow along them, and wherein the opening is visually inspected.

In the following, various preferred embodiments of the invention will be described that can be applied together with any of the filter elements and methods described above.

An elongate cross section of an opening can be characterized by a minimal diameter (defined as the diameter of the largest sphere that can pass through the cross section) and a maximal diameter (defined as the largest distance between any two points on the border of the cross section). In a particular embodiment of the invention, the ratio between said maximal and minimal diameters of the cross section is larger than 2:1, preferably larger than 10:1, and most preferably larger than 100:1. As the particles that are retained are typically (approximately) spherical, the minimal diameter of the cross section will determine the size of the particles that are retained. Thus the aforementioned large ratios between maximal and minimal diameter guarantee that a large fraction of the opening will remain open even when a particle is retained. In this way a high throughput through the filter element can be achieved throughout the whole filtering process.

To achieve sufficiently high flow rates through a filter element, a plurality of (similar designed) openings can be used through which the medium flows in parallel. In case of elongate openings, particularly openings with the aforementioned ratios between maximal and minimal diameter, it is preferred that several (at least two, preferably at least ten, most preferably at least 100) of these openings are spatially arranged in parallel to achieve an optimal exploitation of available area. Moreover, the openings may be arranged with their large dimensions substantially in a common plane. In such an arrangement of parallel openings, the medium is preferably provided from one side of the array and withdrawn from the opposite side and the openings share a common transparent wall.

In a filter element according to the second aspect of the invention, the cross section of the at least one opening may continuously decrease in flow direction (the opening may for example have the three-dimensional shape of a funnel or a wedge). In a preferred embodiment, the cross section decreases however in discrete steps. Retained particles will then automatically be sorted into several size (or type) classes.

The invention further relates to a filter system comprising a filter element according to any of the embodiments described in the application together with additional components for interacting with said filter element and/or the medium inside.

The filter system may for example comprise a (microscope) objective adjacent to the transparent wall of the opening for visual inspection of the opening, particularly for a visual examination of the retained particles by a human observer. Additionally or alternatively, an image sensor may be provided adjacent to the transparent wall for generating an image of the opening. The generated (typically digital) image can then be evaluated by a human observer and/or by automatic image processing routines that are realized by appropriate software. If the opening has an elongated cross section, the objective and/or image sensor is preferably disposed adjacent to its large dimension.

According to another embodiment, at least one marker is provided on the filter element at a known position relative to the opening. By definition, the "marker" shall be designed such that it can readily be detected, for example automatically on an image generated by the aforementioned image sensor. The marker therefore allows to infer the position of the opening (which may not or only hardly be visible) and hence a correct evaluation of the filtering procedure.

In another preferred embodiment, at least one valve element is provided for selectively forwarding medium that has passed the opening. Depending on the setting of this valve, the medium can be led to different destinations. Thus it is for example possible to pass the medium leaving the opening into a waste reservoir during the normal filtering process. After filtering, the setting of the valve element may be changed to allow for an analysis of the retained particles. Retained cells may for example be destroyed and then washed out into particular reaction chambers, where further analysis like PCR can be done. Thermocycling can be done in this stage, too, for example by introducing the filter element into an appropriate thermal controller. The reaction chambers are preferably realized on the same carrier as the filter opening(s), thus allowing the execution of filtering and analysis with one and the same device.

A (micro-) fluidic system may optionally be provided for supplying reagents that shall be mixed with the medium during the filtering process and/or that are needed for a further processing of retained particles after the filtering. If biological cells are retained, the reagents may for example be needed for washing, fixing and/or staining of these cells. It is a particular advantage of the present invention that such a treatment can be done without a need to first transfer retained cells to another location. The fluidic system may particularly comprise a storage for the needed media and/or control elements (valves, pumps etc.) for controlling their flow.

Many assays make use of magnetic particles, for example as labels for target components of the medium, wherein the term "magnetic particle" shall comprise both permanently magnetic particles as well as magnetizable particles, for example superparamagnetic beads. In order to allow for an actuation of such magnetic particles, a filter system according to the invention may comprise a magnet.

The aforementioned magnet may particularly be used to retain magnetic particles (and components bound thereto) within the filter element by magnetic forces, independent of the effect of the opening. Moreover, magnetic particles (typically with attached cells) can be attracted to a wall of the filter element to enhance or enable the filter action. This attraction may be permanent during the filtering procedure or transient, e.g. followed by a release of the magnetic force for further washing purposes. The magnetic actuation can also be used to bring magnetic particles (cells) towards a surface to enhance the specific binding to that surface by capture molecules which are immobilized on the surface. Once bound, the magnetic force may be removed and the unbound elements may be washed away. The "washing" of magnetic particles may be done hydrodynamically (using a wash fluid) and/or magnetically by another magnetic force that pulls magnetic particles away from the filter element.

The opening through which the medium passes, a part of this opening, and/or parts within flow channels that are connected to the opening may preferably comprise binding sites for components (e.g. particles) of the medium. Additionally or alternatively, the aforementioned magnetic particles may comprise such binding sites on their surface. The binding sites may for example be antibodies that specifically bind to target cells of a biological fluid. Thus it is possible to specifically retain and/or capture components even if they are too small to be retained by the opening.

It was already indicated that a plurality of openings may be provided in order to achieve sufficiently high flow rates. Preferably, these openings are connected to a common inlet for the medium and/or to a common outlet that collects the medium after its passage through the openings.

The number of particles that are retained in a single opening depends on the relative sizes of particles and opening, on the density of particles in the medium, and on the total volume of medium that has been filtered. Preferably, these and/or other relevant parameters are adjusted such that on average one particle is retained per opening. This guarantees that each particle can later individually be analyzed. Moreover, in case of elongate openings it is thus guaranteed that flow rates through the openings will only slightly decrease due to the retention of particles.

The invention further relates to a method for filtering a medium in a filter element of the kind described above, said method comprising the following steps:

a) Passing the medium in flow direction through the at least one opening of the filter element such that particles of the medium are retained in said opening.

b) Passing a preparation medium through the at least one opening for treating the retained particles. This treatment may for example comprise a staining or lysis of retained cells.

c) As an optional step, the treated particles may be imaged (at their position in the opening) and/or they may be moved into a separate compartment for further analysis.

Moreover, the invention relates to the use of a filter element of the kind described above for cell-based diagnostics and/or for the isolation of cells of interest from a matrix, for example from blood or another body fluid. The isolation of cells may be part of a diagnostic procedure, or it may serve other purposes (e.g. therapy). Most preferably, the isolation is specific (selective), i.e. only cells of a certain type and/or with certain characteristics (size, rigidity/compliance etc.) are isolated while other cells/components are not. The isolated cells may particularly be rare cells, for example circulating tumor cells. A typical and important field of application of the invention is therefore diagnostics in oncology.

BRIEF DESCRIPTION OF THE DRAWINGS

These and other aspects of the invention will be apparent from and elucidated with reference to the embodiments described hereinafter.

In the drawings.

Like reference numbers or numbers differing by integer multiples of 100 refer in the Figures to identical or similar components.

DETAILED DESCRIPTION OF EMBODIMENTS

Rare cell isolation is of increasing importance for instance for cancer diagnostics based on circulating tumor cells (CTCs). The challenge of such an isolation is the extremely low concentration of these cells amidst a large number of blood cells (erythrocytes and leukocytes) down to 1 cell per 7.5 ml, which needs to be detected.

Circulating tumor cells can differ from leukocytes in their size and stiffness as well as the presence of epithelial cell surface markers (EPCAM). It is possible to isolate CTCs based on specific immune-capture of EPCAM positive cells with antibody-functionalized magnetic beads. CTCs which do not express this marker are thus however not captured.

Cell isolation based on size selection has been proposed by several authors in axial filter systems, i.e. filters in which the fluid flow is essentially perpendicular to the filter surface (cf. G. Vona et al., "Isolation by Size of Epithelial Tumor Cells", American Journal of Pathology, Vol. 156, pp. 57-63, January 2000). Due to the small pore size filters clog easily. For a high throughput the aperture must be high which makes the filters vulnerable and/or expensive to manufacture. The pressure drop over the filter exerts shear stress to the cells which can lead to damage and loss.

Filters can also be used to get rid of excess magnetic beads which are used for immune-capture and otherwise interfere with imaging.

Cells which are captured usually need to be identified by staining and imaging. Complex filter structures interfere with optical imaging. Therefore cells need to be transferred, which is inconvenient.

For molecular analysis one would like to investigate individual cells independently by lysing and RNA expression or DNA rearrangement analysis based on microarrays or sequencing. No practical solutions are known to do this.

In summary, the above approaches have the following drawbacks and problems:
  Limited throughput of filters with well defined pore size.
  Loss of cells which do not express EPCAM.
  Interference of filter structure with optical imaging.
  Impossibility to analyze cells individually after capture.
  Need of manipulation of cells after capture for further identification/analysis.
  Cell damage/rupture due to pressure gradients.

In order to address these problems, a design for a cell capture cartridge will be described below that is based on in-plane filtration with (optional multistep) size selection and marker-specific capture. Captured cells are kept in separate channels to enable separate molecular analysis of individual cells after identification by imaging. No cell transfer is required.

Figure 1:
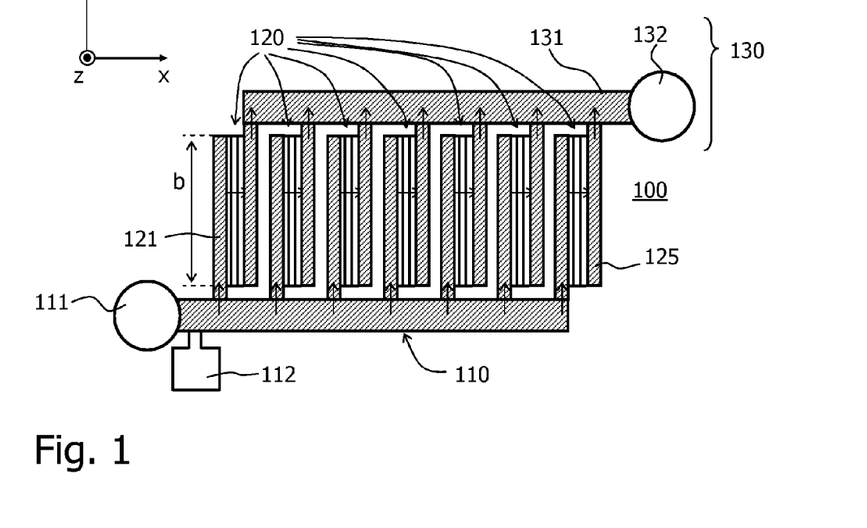
FIG. 1 shows schematically a top view of a filter element according to a first embodiment of the invention.
Figure 2:
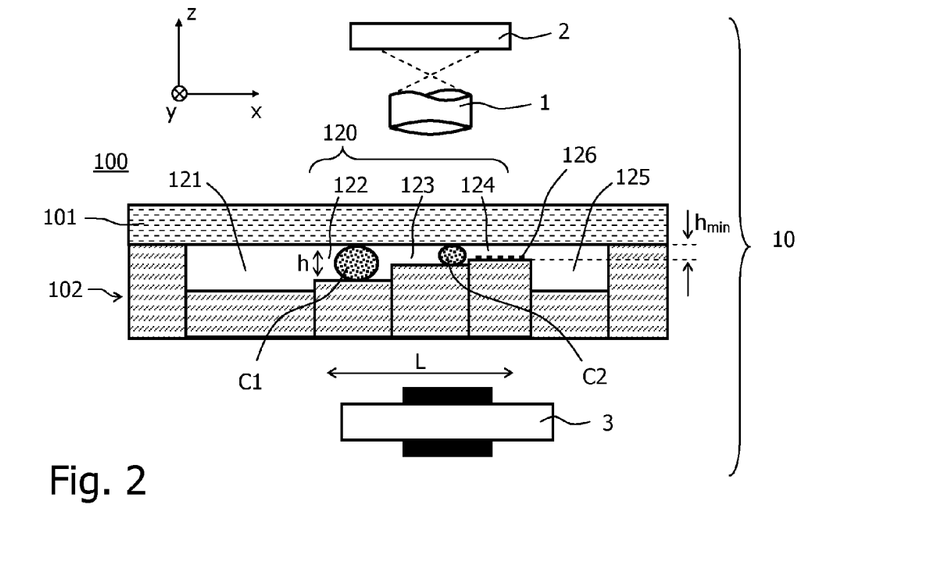
FIG. 2 shows a section in x-direction through an opening of the filter element of FIG. 1, said filter element being part of a filter system.

FIGS. 1 and 2 illustrate an exemplary embodiment of this idea in a top view and a sectional view, respectively. The drawings show a filter element 100 (or cartridge) with a plurality of (here seven identical) elongated openings 120 (also called "gaps" in the following) through which a medium can flow in x-direction (horizontal arrows in FIG. 1). Each opening 120 has an elongate, rectangular cross section extending in the y,z-plane perpendicular to the flow direction. The ratio between the maximal diameter (b in FIG. 1) and minimal diameter (h in FIG. 2) of these cross section, i.e. b:h, preferably ranges between about 100:1 and about 1000:1.

FIG. 2 shows the filter element 100 of FIG. 1 as a part of a filter system 10 comprising additional components 1, 2, 3 needed for the manipulation and/or observation of a sample medium in the filter element. As can be seen from the axial section through one opening 120, the aforementioned cross sections of the openings (which are perpendicular to the drawing plane in FIG. 2) decrease in size in flow direction x. In the shown embodiment, this decrease is caused by a reduction of the height h of the openings, wherein the smallest height $h_{min}$ is also indicated in FIG. 2. Moreover, the decrease in height occurs in the shown example discontinuously in (three) steps, partitioning the opening in three compartments 122, 123, and 124 of different cross sections. Accordingly, larger cells C1 will be retained in the first (largest) compartment 122, while smaller cells C2 manage to enter subsequent smaller compartments 123 or 124 until they get stuck, too.

In order to achieve a significant spatial spread of different cells in x-direction, the length L of the opening 120 (measured in flow direction) is preferably larger than the overall minimal diameter $h_{min}$, for example $L \geq 5 \cdot h_{min}$ or even $L \geq 10 \cdot h_{min}$.

While the Figures show a stepwise narrowing of the openings 120, this narrowing could also be continuous (corresponding to a wedge-shape of the axial cross section in FIG. 2).

In order to achieve a sufficiently high flow rate through the filter element 100, a plurality of openings 120 are connected functionally in parallel. To achieve a compact arrangement, these elongated openings 120 are also spatially arranged in parallel as shown in FIG. 1. The medium to be filtered is provided to the openings 120 by a common inlet channel 110 that begins at an inlet port 111 where the medium can be introduced into the filter element 100. Moreover, distribution channels 121 are sequentially connected to the common inlet channel 110, wherein each distribution channel 121 extends perpendicular to the common inlet channel 110 and distributes the medium to one of the openings 120. The minimal diameters of the cross sections (i.e. the clearance) in the flow path from the sample inlet 111 to the openings 120 shall be larger than the clearance within the openings, such that any particles of interest will be retained in the opening and not earlier.

Each opening 120 ends in an associated collection channel 125, wherein all these collection channels 125 lead into a common outlet channel 131. This common outlet channel 131 extends perpendicular to the collection channels 125 and terminates in an outlet port 132 where medium can be withdrawn from the filter element 100. All channels can thus be connected to a single waste chamber. Again, the clearance of the flow path behind the openings 120 shall be larger than within the openings. Accordingly, the openings constitute a bottleneck in the overall flow path.

With the described repetitive interdigitated stair-like channel structure a very compact design of the filter element 100 is achieved. The flow path in the openings 120 ("analysis areas") with the narrow gap is short for low resistance and is geared to capture only a small number of cells in each channel.

As can be seen from FIG. 2, the filter element 100 is built from a structured bottom element 102 that is covered by a planar top element 101. At least one of these elements, preferably both, is made from a transparent material like glass or plastic to allow for a visual inspection of the interior of the openings 120. In the shown example, the top cover 101 is assumed to be transparent such that the interior of the opening 120 can be visually inspected via an adjacent microscope objective 1. The microscope objective 1 may generate an image on an image sensor 2 which can optionally be evaluated by digital image analysis procedures in a computer (not shown).

The design of the openings is preferably such that all erythrocytes and the vast majority of leukocytes of a blood sample pass through. Therefore only little surface area is required for collecting the target cells. By creating a lateral stair of parallel sections with decreasing gap height, cells which are smaller than the adjacent gap will move into the next section until they get blocked by a gap they cannot enter based on their size and flexibility. In this way always mono layers of cells are created and cells accumulate at the edge of the proximal gap. By having a parallel arrangement the blocking of cells does not affect the overall flow until the edge is covered with cells over the full length.

The length b of the edges can be chosen very large to have a low flow resistance and avoid blocking of the opening. Based on the expected small number of positive cells the number of openings (channels) is chosen such that on average only 1 cell will be captured in each opening 120. In addition areas can be defined in the downstream section which contain e.g. anti-EPCAM capture probes at the (structured) surface to capture also small EPCAM positive cells. FIG. 2 shows such a capture coating 126 in the smallest compartment 124 of the opening 120. Even cells that are equal and/or smaller than the leukocytes can thus be captured if they are EPCAM positive.

The heights h of the openings 120 are chosen to match the cell dimensions to create monolayers enabling imaging analysis (pathology) in-situ, i.e. without cell or filter manipulation. The washing, fixing and staining solutions can be introduced through the same channel system as the sample (i.e. via the inlet port 111 etc.). The in-plane arrangement allows a very effective image analysis (pathology). Stains can be introduced through the same entry port to stain all captured cells in the same way.

In contrast to axial filters with discrete pores the pressure drop due to the flow resistance is not localized at the cell surface, since there is a continuous liquid contact around the cell in the gap. Therefore less cell damage can be expected from this approach.

The imaging optics 1 can recognize the orientation of the analysis area and use that as control for the stepping and imaging approach during analysis. Features can be added to the walls which separate the analysis areas or alternatively features can be present inside the analysis area to provide information about the position of the analysis area with respect to the total filter element 100 (cartridge). This can be a marker like a code or symbol which is interpreted by the image analysis software.

The walls and steps of the openings 120 are integral part of the substrate 102 which can be produced by replication in plastic from a master with the inverse structure, or alternatively by etching in glass. The cover 101 of the cartridge is made from a flat thin sheet of plastic or glass which can be coated on the inner surface with reagents. The substrate and cover are joined for instance by laser or thermal bonding. The resulting filter element 100 can have microscope slide dimensions. Inlet and outlet ports 111, 132 can be integrated for coupling to a system for fluid handling. Additionally or alternatively, reservoirs 112 can be integrated in the device optionally with on-board reagents.

To make the system compatible with approaches that use functionalized magnetic beads, a magnet 3 can be attached. When the sample is mixed with the magnetic beads before injection, cells with attached beads will be pulled to the channel walls or the bottom of the openings and stay there as long as the magnetic field is on. This allows an additional way of collecting cells which are validated already. The result of this capture can be compared in situ in the same cartridge and single scan with the size-based capture in the stair channels and (if included) the capture by antibodies which are immobilized on the channel surface.

The aforementioned attraction of magnetic particles (and cells attached thereto) may optionally be followed by a release of the magnetic force for further washing purposes. Additionally, magnetic forces may be used to actively remove unbound beads away from the binding surface before the assay is evaluated.

Yet another embodiment can make use of biotinylized capture probes which bind to the cells and are then captured by streptavidin functionalized surfaces in the cartridge.

In order to be able to analyze captured cells for their molecular characteristics, on the exit side of the openings a valve may be included which allows to close the common waste access, and instead opens individual exits for access to analysis chambers in which for instance microarray hybridizations and/or PCR reactions can be performed.

Figure 3:
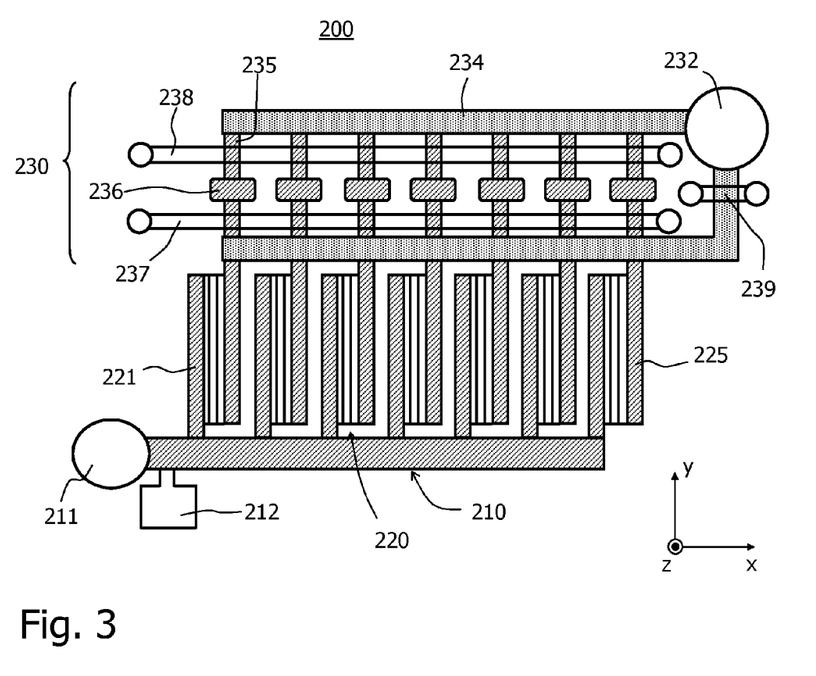
FIG. 3 shows a top view onto a second embodiment of a filter element comprising a plurality of reaction chambers for further analysis of retained particles.

FIG. 3 shows a filter element 200 according to the aforementioned embodiment. Components that are similar or identical to those of the first embodiment (FIGS. 1, 2) need not be explained again. The novel feature of the filter element 200 is the design of the outlet structure 230:

The collection channels 225 of the openings 220 are connected to a common outlet channel 231 that leads to an outlet port 232. Each collection channel 225 is now however also connected to an associated reaction chamber 236. The outlets of these reaction chambers 236 are connected to a common waste collection channel 234 that ends at the outlet port 232.

Moreover, it can be seen that a valve mechanism is provided for controlling the flow through the aforementioned channels. A first valve system 237 controls the connection between the collection channels 225 and the reaction chambers 236. A second valve system 238 controls the connections between the reaction chambers 236 and the common waste collection channel 234. A third valve 239 controls the connection between the common outlet channel 231 and the outlet port 232. The valve systems 237, 238, and 239 can for instance be realized by pneumatic control lines which act as valves for the associated fluidic channels.

By appropriately actuating (i.e. opening and closing) the valve systems 237, 238, and 239, the medium leaving the openings 220 can selectively be forwarded either directly to the outlet port 232 (third valve 239 open and first valves 237 closed) or to the individual reaction chambers 236 (third valve 239 closed and first valves 237 open). While the first alternative is preferably used during the filtering process, the latter is used after filtering for an analysis of the retained particles in the reaction chambers 236.

Since the number of openings 220 is chosen to match the maximum number of captured cells, in fact the molecular (genetic) properties of every cell can be determined without further manipulation. The reaction chambers 236 can contain microarrays for specific hybridization of RNA, or DNA. Amplification reactions can be carried out after introducing PCR mix to the crude lysate of the cells. It is clear that the design of the downstream part can be modified to accommodate the necessary reaction steps. Thermocycling can be done for amplification by introducing the cartridge in the appropriate thermal controller. The substrate is compatible with fluorescence detection for reading microarrays and monitoring qPCR.

One can also choose for pooling or excluding cells in reaction chambers, based on the pathological analysis of the captured cells, which allows interpretation and identification of false positive cells and a direct coupling of the pathology to the genetics.

The dimensions of the filter element can be adjusted for different diagnostic applications. For instance for small cell lung cancer it is known that the CTCs are very large. For other applications where the cell sizes are closer a closer spacing of the gap heights is required. The ideal gap heights can be determined experimentally before use in diagnostic application. In the minimum scenario the filter would only be used to separate free magnetic beads from captured cells after immune-capture without further specific separation of the cells and in addition for the benefit of creating a monolayer for identification with staining and pathological investigations.

Regarding scaling of the design, a first parameter to be considered is the flow resistance in relation to the flow rate. The flow rate is derived from the sample volume and desired analysis time. In a gap the pressure drop $\Delta p_v$ scales as follows (with η being the viscosity and V being the velocity of the medium):

$$\Delta p_v = \frac{12\eta LV}{h^2}$$

One would like to keep the height, h, as large as possible, but that is given by the size of the cells which need to be captured. So one can only try to reduce the length, L, as much as possible and likewise increase the width, which is not included in the equation above as it is valid for an infinitely wide channel. The volume flow rate Q is V·A, with A the cross section of the channel (=b·h).

For a volume flow rate Q of 10 ml in 16 minutes (Q=10 μl/s) in a channel of total width of b=10 mm the shear rate in the gap would become $10^4$ $s^{-1}$ and the pressure drop $10^7$ Pa/m. This creates a risk that the cells might be damaged. Therefore it is preferred to increase the channel width further. This is achieved by creating multiple channels with a lateral flow as illustrated in FIG. 1. In this way a channel width of n times 1 cm can be realized on a microscope slide surface. n can be from 10 up to several 100 with a proportional reduction in flow rate and pressure drop.

Cell damage due to strong pressure gradients are a concern in conventional filters. The present invention provides a gap so that continuity of the fluid is always preserved up to complete blocking of the gap.

In a conventional filter a captured cell will seal off a pore completely so that the pressure inside the pore will be lower than on top of it (the pressure difference is due to the pressure drop due to flow in the neighboring, still open pores). Once all pores are filled the pressure drop will be equal to the applied pressure at the entrance. This pressure difference will occur in a very small region where the cell membrane makes contact to the pore of the filter. This local gradient can rupture the cell membrane.

In the proposed filter system the elongated opening is not sealed off by the cell so that the pressure drop remains moderate and continuous over the cell membrane. It is equal to the pressure drop in the wider channel due to flow.

Regarding the manufacturing of the proposed filter element, cover 101 and substrate 102 can be joined permanently by a bonding technology, like laser welding or other, or alternatively just be in contact with each without permanent bonding. Contact areas can be pretreated to enhance the sticking of the cover to the substrate.

The entrance region for filling the blood can be designed such that convenient filling is enabled, e.g. by providing a through hole (inlet port) and optionally a cap which can be closed after filling. Reagents can be provided in dry form in the entrance region. At the end of the venting channel a waste reservoir can be included to avoid possible spilling of excess of sample (e.g. blood).

The structured substrates 102 can be manufactured by injection molding or other replication technology. The master structure which is required as a mold can be produced with the aid of photolithography and/or etching. One possible approach requires two lithographic masks. The first one contains the analysis areas (i.e. the openings 120, 220). In a second step a mask representing the channel structure is used in order to create a resist pattern which is used for the selective etching of the substrate (e.g. silica). After etching the etch resist is stripped and the photopolymer on the analysis areas remains on the substrate. In this way three levels are created on the substrate. This substrate can then be copied into a Ni shim by electroplating in a way which is well established for instance in optical disc manufacturing. The Ni shim is then used as an insert in the mold for replication in plastic by molding.

Alternatively, etching in glass can be used to create the stepwise channels with precisely defined gaps.

At the inlet and outlet of the filter structures reservoirs can be attached or integrated which allow interconnecting to fluidic tubing or syringes or fluid handling stations, as well as for storing reagents and waste. Pumping of the reagents can be done by external pumps, pneumatic interfaces, or other integrated pumps.

Experiments

Figure 4:
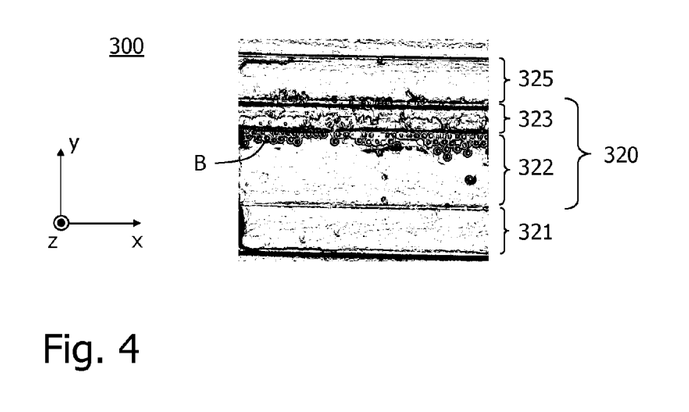
FIG. 4 shows a photograph of a filter element after 15 minutes of filtering a medium with polystyrene beads and THP1 cells.

According to FIG. 4, a test medium was filtered in a staircase filter element 300 (similar in design to that shown in FIGS. 1 and 2, but with only two steps 322, 323). 15 μm polystyrene beads (Phosphorex) at a concentration of $1.6·10^5$ beads/ml PBS and THP1 cells at a concentration of $1.2·10^6$ cells/ml PBS were mixed. The resulting medium contained $8·10^4$ beads and $6·10^5$ THP1 cells per ml PBS. This medium was led through the staircase filter at 0.2 ml/min.

The results were analyzed in a FACS (Fluorescence Assisted Cell Sorting) machine to investigate the relative amounts of beads and THP1 cells present after the filtering process. The data shows that the filter does not let any beads pass through.

FIG. 4 shows a photograph of the filter element 300. It can be seen that some cells are stuck in the narrowest slit 323 or are caught by the beads B which effectively form a filter with a small pore size. Pretreatment of the device may reduce the adhesion of cells.

In summary, a new filter structure is designed for efficient isolation of rare cells from a complex matrix like blood. It allows a high throughput (large volume) and presents the cells in a single plane on an optical substrate for direct inspection (pathology) and for further molecular diagnostics on individual cells without the need for handling. The device makes use of a narrowing (e.g. stair-like) parallel channel structure which can be made readily by injection molding or glass etching. It is compatible with scanners used in pathology, e.g. for digitizing images. The isolation can be size- and surface marker based. Pressure gradients are smaller than in conventional filters to avoid cell damage. The filter structure can be applied in cell-based diagnostics, in particular rare cells in blood with circulating tumor cells as the most important example.

While the invention has been illustrated and described in detail in the drawings and foregoing description, such illustration and description are to be considered illustrative or exemplary and not restrictive; the invention is not limited to the disclosed embodiments. Other variations to the disclosed embodiments can be understood and effected by those skilled in the art in practicing the claimed invention, from a study of the drawings, the disclosure, and the appended claims. In the claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A filter element for retaining components of a medium flowing in a flow direction through at least one opening, wherein said opening
    is a bottleneck in a flow path of the medium wherein the flow path is wider in front and behind the bottleneck;
    has an elongate cross section, measured perpendicular to the flow direction, that decreases along an extended length of the opening in the flow direction; and
    is bordered by a transparent wall.

2. The filter element according to claim 1, wherein said opening has an elongate cross section with a ratio between a maximal diameter and a minimal diameter of said cross section being larger than 2:1.

3. The filter element according to claim 1, wherein said opening has a cross section with a minimal diameter that decreases in flow direction by more than about 20%.

4. The filter element according to claim 1, wherein at least two openings are arranged in parallel.

5. The filter element according to claim 1, wherein minimal diameter of the cross section of the opening decreases in at least one step.

6. The filter element according to claim 1, wherein at least one valve is provided for selectively forwarding the medium leaving the opening to different destinations.

7. The filter element according to claim 1, wherein a fluidic system is provided for supplying reagents to the filter element that mix with the medium and/or that are needed for a further processing of retained particles.

8. A filter system comprising a filter element according to claim 1,
    an objective lens and/or an image sensor is provided adjacent to the opening of the filter element.

9. A filter system comprising a filter element according to claim 1,
    wherein a magnet is provided for actuating magnetic particles of the medium in the filter element.

10. The filter system of claim 9, wherein a magnet is used for attracting magnetic particles of the medium at least transiently to a wall of the opening.

11. The filter element according to claim 1, wherein the opening or a part thereof, or a part within associated flow channels, or at least one magnetic particle of the medium comprises specific binding sites for components of the medium.

12. A method for filtering a medium in a filter element according to claim 1, wherein:
    a) the medium is passed in a flow direction through the at least one opening such that particles of the medium are retained in said opening, wherein said opening is a bottleneck in a flow path of the medium wherein the flow path is wider in front and behind the bottleneck, said opening having an elongate cross section, measured perpendicular to the flow direction, that decreases along an extended length of the opening in the flow direction;
    b) a preparation medium is passed through the at least one opening for treating the retained particles;
    c) treated particles are imaged and/or moved into a separate compartment for further analysis.

13. A method for cell-based diagnostics and/or for the isolation of cells comprising the steps of filtering a medium by using the filter element according to claim 1; and
    performing at least one diagnostic procedure on cells from the medium that are retained on the filter element and/or isolating the cells from the medium that are retained on the filter element.

14. A method for filtering particles out of a medium by retaining them in at least one opening through which said medium passes in a flow direction,
    wherein said opening is a bottleneck in a flow path of the medium in which the flow path is wider in front and behind the bottleneck, said opening having an elongate cross section, measured perpendicular to the flow direction, that decreases along an extended length of the opening in the flow direction;
    wherein the particles are retained at different positions in the flow direction which correspond to a property of said particles.

15. The method according to claim 14, wherein said at least one opening is optically inspected from a direction substantially perpendicular to the flow direction of the medium.

* * * * *